(12) United States Patent
Chang et al.

(10) Patent No.: US 10,891,845 B2
(45) Date of Patent: Jan. 12, 2021

(54) MOUTH AND NOSE OCCLUDED DETECTING METHOD AND SYSTEM THEREOF

(71) Applicant: NATIONAL YUNLIN UNIVERSITY OF SCIENCE AND TECHNOLOGY, Yunlin County (TW)

(72) Inventors: Chuan-Yu Chang, Yunlin County (TW); Fu-Jen Tsai, New Taipei (TW)

(73) Assignee: NATIONAL YUNLIN UNIVERSITY OF SCIENCE AND TECHNOLOGY, Yunlin County (TW)

(*) Notice: Subject to any disclaimer, the term of this patent is extended or adjusted under 35 U.S.C. 154(b) by 85 days.

(21) Appl. No.: 16/202,108

(22) Filed: Nov. 28, 2018

(65) Prior Publication Data

US 2020/0168071 A1 May 28, 2020

(51) Int. Cl.
*G08B 21/04* (2006.01)
*A61B 5/00* (2006.01)
(Continued)

(52) U.S. Cl.
CPC ........ *G08B 21/0476* (2013.01); *A61B 5/0077* (2013.01); *G06K 9/00248* (2013.01); *G06K 9/00255* (2013.01); *G06K 9/6217* (2013.01); *G06T 7/0014* (2013.01); *G06T 7/90* (2017.01); *G16H 30/20* (2018.01); *G06T 2207/20081* (2013.01); *G06T 2207/20084* (2013.01);
(Continued)

(58) Field of Classification Search
CPC .............................. G08B 21/0476; G06T 7/90
See application file for complete search history.

(56) References Cited

U.S. PATENT DOCUMENTS

| 8,406,525 B2* | 3/2013 | Ma ..................... G06K 9/00275 |
| | | 382/159 |
| 10,621,477 B2* | 4/2020 | Wolf ..................... G06K 9/6257 |
| 2019/0090774 A1* | 3/2019 | Yang ..................... A61B 6/032 |

FOREIGN PATENT DOCUMENTS

| CN | 106874883 A | 6/2017 |
| CN | 207916933 U | 9/2018 |

(Continued)

OTHER PUBLICATIONS

Kavin, "[Note] Deep Learning—Convolutional Neural Network", iThelp, published on Sep. 13, 2018, webpage, accessed at https://ithelp.ithome.com.tw/articles/10199130, Taiwan, R.O.C.
(Continued)

*Primary Examiner* — Tuan H Nguyen
(74) *Attorney, Agent, or Firm* — CKC & Partners Co., LLC

(57) ABSTRACT

A mouth and nose occluded detecting method includes a detecting step and a warning step. The detecting step includes a facial detecting step, an image extracting step and an occluded determining step. In the facial detecting step, an image is captured by an image capturing device, wherein a facial portion image is obtained from the image. In the image extracting step, a mouth portion is extracted from the facial portion image so as to obtain a mouth portion image. In the occluded determining step, the mouth portion image is entered into an occluding convolutional neural network so as to produce a determining result, wherein the determining result is an occluding state or a normal state. In the warning step, a warning is provided according to the determining result.

14 Claims, 6 Drawing Sheets

(51) Int. Cl.
  *G06T 7/00*    (2017.01)
  *G06K 9/00*    (2006.01)
  *G16H 30/20*   (2018.01)
  *G06T 7/90*    (2017.01)
  *G06K 9/62*    (2006.01)

(52) U.S. Cl.
  CPC .............. *G06T 2207/30004* (2013.01); *G06T 2207/30201* (2013.01)

(56) References Cited

FOREIGN PATENT DOCUMENTS

| | | |
|---|---|---|
| CN | 208092911 U | 11/2018 |
| TW | 200933535 A | 8/2009 |
| TW | 201832134 A | 9/2018 |
| WO | 2017183034 A1 | 10/2017 |

OTHER PUBLICATIONS

Facial Detection—MTCNN (Multi-task Cascaded Convolutional Networks), Er-Wen Guo, YouTube Video, published Jan. 22, 2018, accessed at https://www.youtube.com/watch?v=zZZcEu-iZnk; segment from 0:00 to 2:55.

* cited by examiner

300

310

MOUTH AND NOSE OCCLUDED DETECTING METHOD AND SYSTEM THEREOF

BACKGROUND

Technical Field

The present disclosure relates to a mouth and nose occluded detecting method and system thereof. More particularly, the present disclosure relates to a mouth and nose occluded detecting method and system thereof according to a convolutional neural network.

Description of Related Art

Because of the protector cannot always stay with the patient, and in order to avoid the patient be choked by mouth occluding or nose occluding, an occluded detection system usually be utilized to assist the protector so as to reduce the burden. However, a misjudgment from conventional occluded detection systems is usually occurred due to a light from an environment or a color of a cloth from the patient.

Hence, how to avoid the light from the environment or the color of the cloth affect the mouth and nose occluded detecting system is a target of the industry.

SUMMARY

According to one embodiment of the present disclosure, a mouth and nose occluded detecting method includes a detecting step and a warning step. The detecting step includes a facial detecting step, an image extracting step and an occluded determining step. In the facial detecting step, an image is captured by an image capturing device, wherein a facial portion image is obtained from the image according to a facial detection. In the image extracting step, a mouth portion is extracted from the facial portion image according to an image extraction so as to obtain a mouth portion image. In the occluded determining step, the mouth portion image is entered into an occluding convolutional neural network so as to produce a determining result, wherein the determining result is an occluding state or a normal state. In the warning step, a warning is provided according to the determining result, when the determining result is the normal state, the detecting step is performed, when the determining result is the occluding state, the warning is provided.

According to another embodiment of the present disclosure, a mouth and nose occluded detecting system includes an image capturing device, a processor and a warning device. The image capturing device is for capturing an image. The processor is electronically connected to the image capturing device, and includes a facial detecting module, an image extracting module and an occluded determining module. The facial detecting module is electronically connected to the image capturing device, wherein the facial detecting module captures the image by the image capturing device, and a facial portion image is obtained from the image according to a facial detection. The image extracting module is electronically connected to the facial detecting module, wherein the image extracting module extracts a mouth portion from the facial portion image according to an image extraction so as to obtain a mouth portion image. The occluded determining module is electronically connected to the image extracting module, wherein the occluded determining module enters the mouth portion image into an occluding convolutional neural network so as to produce a determining result. The warning device is signally connected to the processor, wherein the warning device provides a warning according to the determining result, when the determining result is a normal state, a determining step is performed, when the determining result is an occluding state, the warning is provided.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiment will be described with the drawings. For clarity, some practical details will be described below. However, it should be noted that the present disclosure should not be limited by the practical details, that is, in some embodiment, the practical details is unnecessary. In addition, for simplifying the drawings, some conventional structures and elements will be simply illustrated, and repeated elements may be represented by the same labels.

Figure 1:
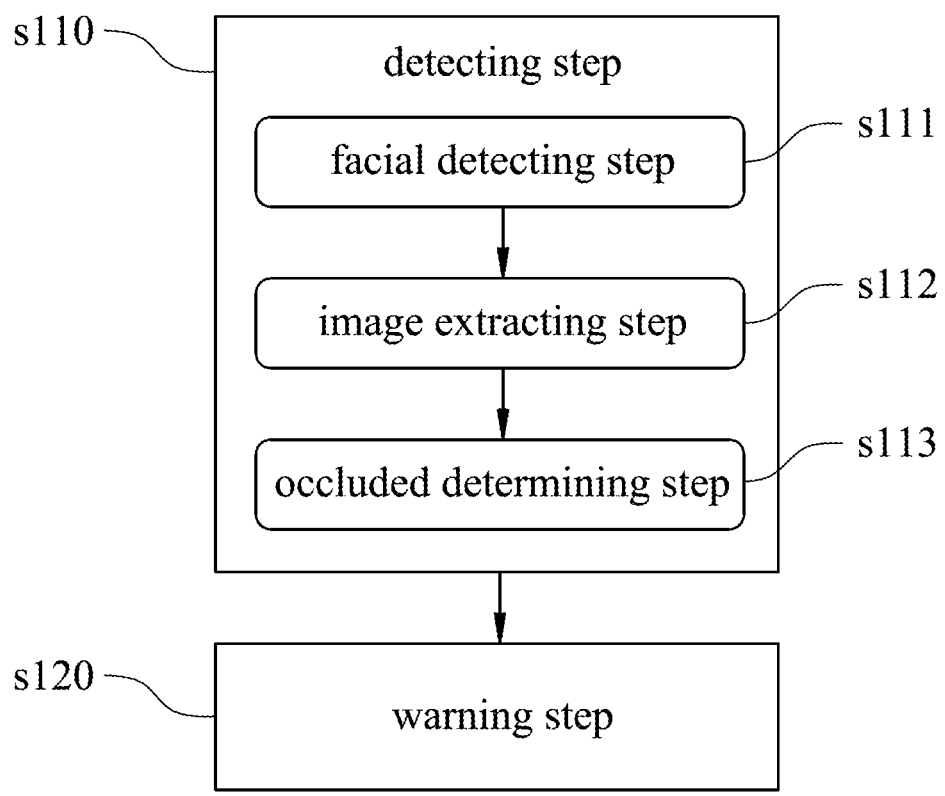
FIG. 1 is a step flow chart of a mouth and nose occluded detecting method according to one embodiment of the present disclosure.

FIG. 1 is a step flow chart of a mouth and nose occluded detecting method s100 according to one embodiment of the present disclosure. In FIG. 1, the mouth and nose occluded detecting method s100 includes a detecting step s110 and a warning step s120.

In detail, the detecting step s110 includes a facial detecting step s111, an image extracting step s112 and an occluded determining step s113. In the facial detecting step s111, an image is captured by an image capturing device 410 (shown in FIG. 6), wherein a facial portion image is obtained from the image according to a facial detection. In the image extracting step s112, a mouth portion is extracted from the facial portion image according to an image extraction so as to obtain a mouth portion image 310 (shown in FIG. 5). In the occluded determining step s113, the mouth portion image 310 is entered into an occluding convolutional neural network so as to produce a determining result, wherein the determining result is an occluding state or a normal state. In the warning step s120, a warning is provided according to the determining result. When the determining result is the normal state, the detecting step s110 is performed so as to monitor a state of a patient, continuously. When the determining result is the occluding state, the warning is provided so as to notify a protector to treatment, expeditiously. Therefore, whether the mouth and the nose of patient are occluded by foreign matters is determined by entering the mouth portion image 310 into the occluding convolutional neural network so as to avoid the occluding convolutional neural network provides a misjudgment because of an influence form an environmental factor, wherein the environmental factor is a light from an environment or a color of a cloth from the patient.

Figure 2:
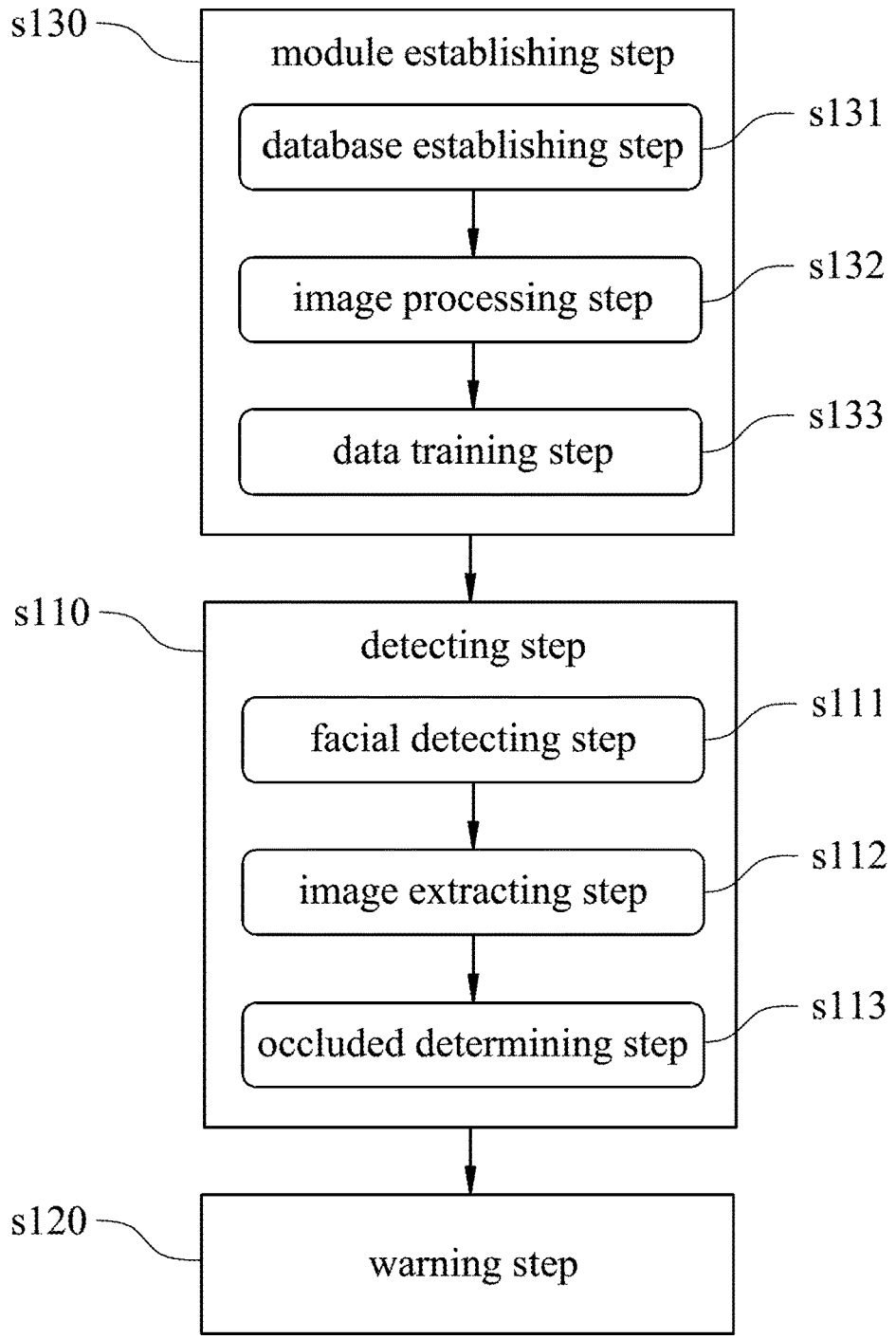
FIG. 2 is a step flow chart of a mouth and nose occluded detecting method according to another embodiment of the present disclosure.

FIG. 2 is a step flow chart of a mouth and nose occluded detecting method s100 according to another embodiment of the present disclosure. In FIG. 2, the mouth and nose occluded detecting method s100 includes a detecting step s110, a warning step s120 and a module establishing step s130.

In FIG. 1 and FIG. 2, the detecting step s110 and the warning step s120 of the embodiment in FIG. 2 are same with the detecting step s110 and the warning step s120 of the embodiment in FIG. 1, and will not be described again herein. It should be mentioned, the mouth and nose occluded detecting method s100 of the embodiment in FIG. 2 further includes the module establishing step s130. The module establishing step s130 includes a database establishing step s131, an image processing step s132 and a data training step s133. In the database establishing step s131, an occluding detection database is established and includes a plurality of occluding images and a plurality of normal images, wherein the plurality of occluding images include a plurality of blanket occluding images and a plurality of regurgitation milk occluding images. In the image processing step s132, a post-processing occluded detection image is obtained from each of the occluding images or each of the normal images according to an image procession, and the post-processing occluded detection image is stored into the occluding detection database. In the data training step s133, the occluding convolutional neural network is trained by the post-processing occluded detection images, the occluding images and the normal images in the occluding detection database. Therefore, a number of the training samples of the occluding convolutional neural network are increased by obtaining the post-processing occluded detection images from separately processing the occluding images and the normal images so as to increase the determining accuracy rate of the occluding convolutional neural network.

In order to increase the number of the training samples of the occluding convolutional neural network, the image procession of the image processing step s132 can be an image flipping, a histogram equalization, a log transform, a gamma processing or a Laplace processing. A target of image processing the occluding images is for simulating an illuminance of the image and a profile of the image in various situations so as to train the occluding convolutional neural network. The histogram equalization is for evenly renewing the distribution of the brightness of the occluding image so as to increase the brightness of a dark portion in the occluding image and decrease the brightness of a bright portion in the occluding image. The log transformation is for increasing the brightness of the dark portion in the occluding image. The gamma processing is for increasing the brightness of the dark portion in the occluding image and decreasing the brightness of the bright portion in the occluding image by adjusting a gamma value of the occluding image. The Laplace processing is for obtaining an image profile, an image shape and a distribution status of the occluding image by a second order partial differential. In the other word, the occluding image can be processed by each of the histogram equalization, the log transform, the gamma processing and the Laplace processing, and the occluding image can be processed by the image flipping and then processed by each of the histogram equalization, the log transform, the gamma processing and the Laplace processing for obtaining the nine post-processing occluded detection images so as to increase the number of the training samples of the occluded convolutional neural network. It should be mentioned, the image procession disclosures above, but it should not be limited to the description of the embodiments herein. Table 1 shows an accuracy rate of a first example and an accuracy rate of a first comparative example, wherein an occluded convolutional neural network structure 200 (shown in FIG. 3) of the first example is same with an occluded convolutional neural network structure of the first comparative example. The difference between the first example and the first comparative example is the number of the training samples of the first example greater than the number of the training samples of the first comparative example, wherein the training samples of the first example are the occluding images, the normal images and the post-processing occluded detection images, and the training samples of the first comparative example are the occluding images and the normal images. In Table 1, the accuracy rate of the first comparative example is 84% and the accuracy rate of the first example is 94%. That is, in the module establishing step s130, when the number of the training samples of the occluded convolutional neural network is increased, the accuracy rate of an occluded convolutional neural network is increased.

TABLE 1

| | Training sample | Accuracy rate |
|---|---|---|
| first example | occluding images, normal images and post-processing occluded detection images | 94% |
| first comparative example | occluding images and normal images | 84% |

Figure 3:
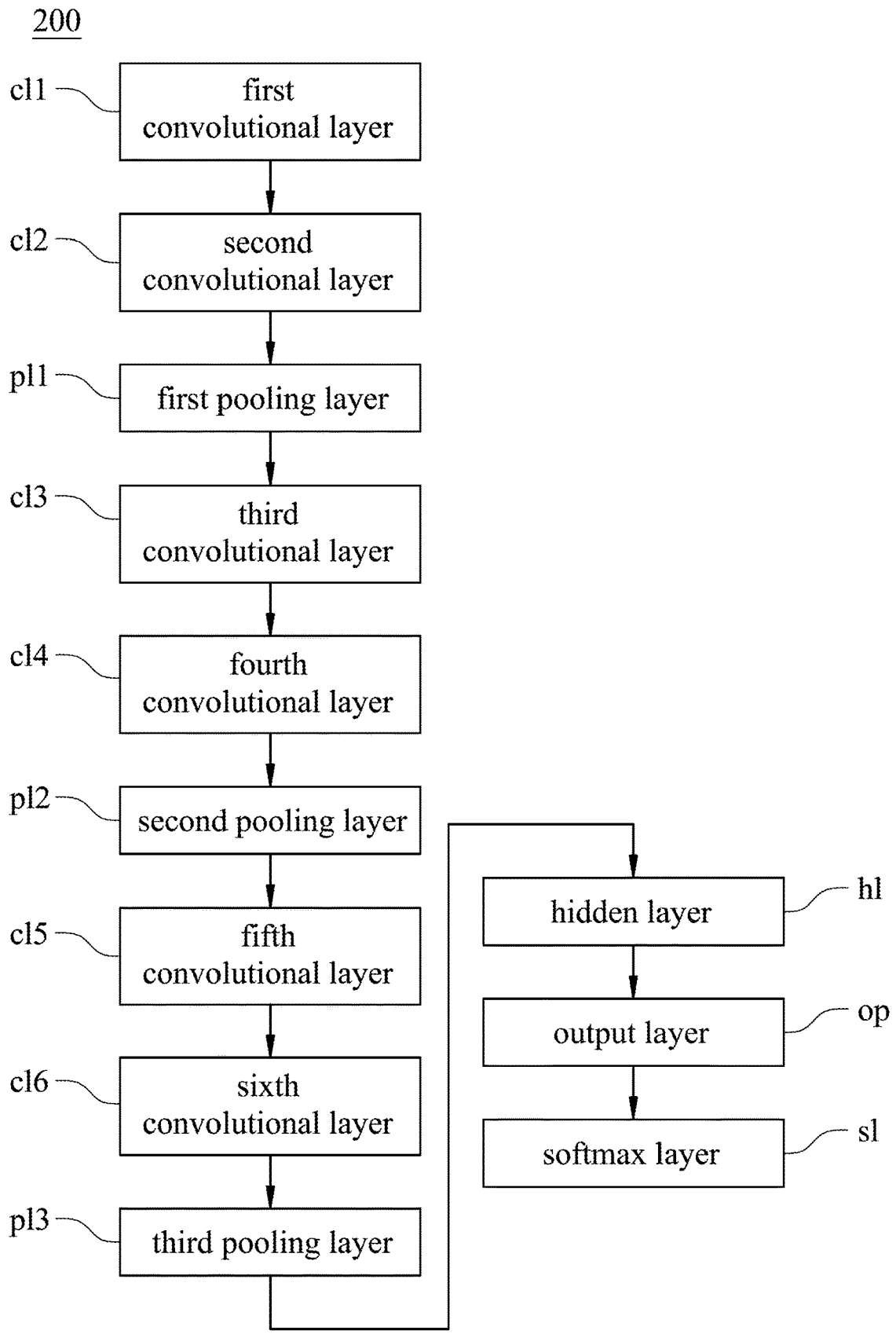
FIG. 3 is a schematic chart of an occluded convolutional neural network structure of the mouth and nose occluded detecting method according to the embodiment of FIG. 1.

FIG. 3 is an occluded convolutional neural network structure 200 of the mouth and nose occluded detecting method s100 according to the embodiment of FIG. 1, and Table 2 shows the list of the occluded convolutional neural network structure 200 of FIG. 3. In FIG. 3 and Table 2, the occluded convolutional neural network includes six convolutional layers (its reference numeral is omitted), three pooling layers (its reference numeral is omitted), a hidden layer hl and an output layer op, in detail, the convolutional layers include a first convolutional layer cl1, a second convolutional layer cl2, a third convolutional layer cl3, a fourth convolutional layer cl4, a fifth convolutional layer cl5 and a sixth convolutional layer cl6. The first convolutional layer cl1 and the second convolutional layer cl2 are conv3_16 which means a kernel size of the first convolutional layer cl1 and a kernel size of the second convolutional layer cl2 are 3×3, and an output feature maps number of the first convolutional layer cl1 and an output feature maps number of the second convolutional layer cl2 are 16. The third convolutional layer cl3 and the fourth convolutional layer cl4 are conv3_32 which means a kernel size of the third convolutional layer cl3 and a kernel size of the fourth convolutional layer cl4 are 3×3, and an output feature maps number of the third convolutional layer cl3 and an output feature maps number of the fourth convolutional layer cl4 are 32. The fifth convolutional layer cl5 and the sixth convolutional layer cl6 are conv3_64 which means a kernel size of the fifth convolutional layer cl5 and a kernel size of the sixth convolutional layer cl6 are 3×3, and an output feature maps number of the fifth convolutional layer cl5 and an output feature maps number of the sixth convolutional layer cl6 are 64. In addition, each of the convolutional layers includes a plurality of kernels so as to output a plurality of feature maps, wherein a size of each of the kernels is 3×3, a stride of each of the kernels is 1, and each of the convolutional layers adjusts a size of each of the feature maps according to a padding method. In detail, a post-padding image is obtained from the image by a padding method before perform a convolution operation of each of the convolutional layers, and then performing the convolution operation according to the post-padding image, wherein a size of the image is 50×50, a size of the post-padding image is 52×52, and the padding method is a zero padding method. The pooling layers include a first pooling layer pl1, a second pooling layer pl2 and a third pooling layer pl3, each of the pooling layers utilizes a max pooling method and includes a pooling filter, wherein a size of the pooling filter is 2×2 and a stride of the pooling filter is 2. The hidden layer hl includes a first fully connecting layer, wherein the first fully connecting layer is FC_128 which means a neuron number of the first fully connecting layer is 128. The output layer op includes a second fully connecting layer, wherein the second fully connecting layer is FC_2 which means a neuron number of the second fully connecting layer is 2.

TABLE 2

| First convolution layer | Conv3_16 |
| Second convolution layer | Conv3_16 |
| First pooling layer | Max pooling method |
| Third convolution layer | Conv3_32 |
| Fourth convolution layer | Conv3_32 |
| Second pooling layer | Max pooling method |
| Fifth convolution layer | Conv3_64 |
| Sixth convolutional layer | Conv3_64 |
| Third pooling layer | Max pooling method |
| Hidden layer | FC_128 |
| Output layer | FC_2 |

The occluded convolutional neural network structure 200 can further include a softmax layer sl, wherein the softmax layer sl is for calculating a probability of the occluding state and a probability of the normal state so as to produce the determining result. The softmax layer sl includes at least one image state, a number of the image state, the mouth portion image 310, at least one image state parameter, at least one image state probability and an image state probability set, wherein $y^{(i)}$ is the image state, k is the number of the image state, $x^{(i)}$ is the mouth portion image 310, θ is an image state parameter set, each of $\theta_1, \theta_2, \ldots, \theta_K$ is the image state parameter, $p(y^{(i)}=k|x^{(i)}:\theta)$ is the image state probability, $h_\theta(x^{(i)})$ is the image state probability set and T means transpose matrix. The softmax layer sl is corresponded by formula (1).

$$h_\theta(x^{(i)}) = \begin{bmatrix} p(y^{(i)} = 1 \mid x^{(i)}; \theta) \\ p(y^{(i)} = 2 \mid x^{(i)}; \theta) \\ \vdots \\ p(y^{(i)} = k \mid x^{(i)}; \theta) \end{bmatrix} = \frac{1}{\sum_{j=1}^{k} e^{\theta_j^T x^{(i)}}} \begin{bmatrix} e^{\theta_1^T x^{(i)}} \\ e^{\theta_2^T x^{(i)}} \\ \vdots \\ e^{\theta_k^T x^{(i)}} \end{bmatrix}. \quad \text{formula (1)}$$

Therefore, the occluded convolutional neural network is for determining a probability of each of the image state of the mouth portion image 310, wherein the image state at least for the occluding state and the normal state. When the probability of the occluding state is greater than the probability of the normal state, the determining result is the occluding state. When the probability of the normal state is greater than the probability of the occluding state, the determining result is the normal state.

Table 3 shows an occluded convolutional neural network structure 200 of a second example and an occluded convolutional neural network structure of a second comparative example, a third comparative example, a fourth comparative example, a fifth comparative example and a sixth comparative example, respectively. Table 4 shows an accuracy of the occluded convolutional neural network of the second example and an accuracy of the occluded convolutional neural network of the second comparative example, the third comparative example, the fourth comparative example, the fifth comparative example and the sixth comparative example, respectively. In Table 3 and Table 4, the accuracy of the occluded convolutional neural network of the second example is greater than the accuracy of the occluded convolutional neural network of the second comparative example, the third comparative example, the fourth comparative example, the fifth comparative example and the sixth comparative example, respectively.

TABLE 3

| Second comparative example | Third comparative example | Fourth comparative example | Fifth comparative example | Sixth comparative example | Second example |
|---|---|---|---|---|---|
| Conv3_16 | Conv3_16 | Conv3_32 | Conv3_32 | Conv3_16 | Conv3_16 |
| | Conv3_16 | Conv3_32 | Conv3_32 | Conv3_16 | Conv3_16 |
| | | First pooling layer | | | |
| Conv3_32 | Conv3_32 | Conv3_64 | Conv3_64 | Conv3_32 | Conv3_32 |
| | Conv3_32 | Conv3_64 | Conv3_64 | Conv3_32 | Conv3_32 |
| | | Second pooling layer | | | |
| | | | Conv3_128 | Conv3_64 | Conv3_64 |
| | | | Conv3_128 | Conv3_64 | Conv3_64 |
| | | | | Conv3_64 | |
| | | | | Third pooling layer | |
| | | | FC_128 | | |
| | | | FC_2 | | |
| | | | Softmax layer | | |

TABLE 4

| | Accuracy rate |
|---|---|
| Second comparative example | 88% |
| Third comparative example | 88% |
| Fourth comparative example | 91% |
| Fifth comparative example | 92% |
| Sixth comparative example | 92% |
| Second example | 94% |

In order to obtain the facial portion image from the image, the facial detection can utilize a Multi-task cascaded convolutional network for detecting a facial portion of the image, wherein the Multi-task cascaded convolutional network includes a Proposal-Net (P-Net), a Refine-Net (R-Net) and an Output-Net (O-Net). The Proposal-Net obtains a plurality of bounding box by a Proposal-Net convolutional neural network. The Refine-Net removes a non-facial bounding box by a Refine-Net convolutional neural network. The Output-Net outputs a facial feature by an Output-Net convolutional neural network. Therefore, the facial portion image is obtained by entering the image into the Multi-task cascaded convolutional network.

Figure 4:
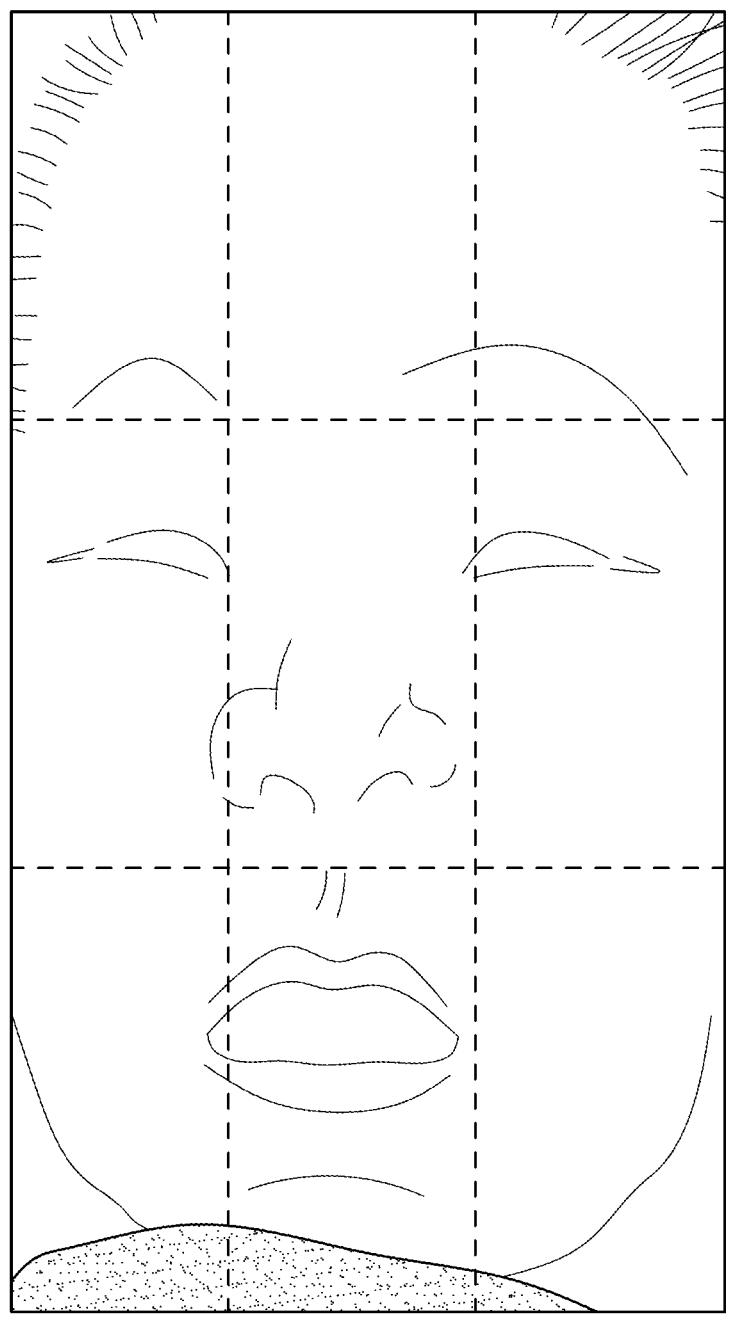
FIG. 4 is a schematic diagram of a nine-square facial portion image of the mouth and nose occluded detecting method according to the embodiment of FIG. 1.
Figure 5:
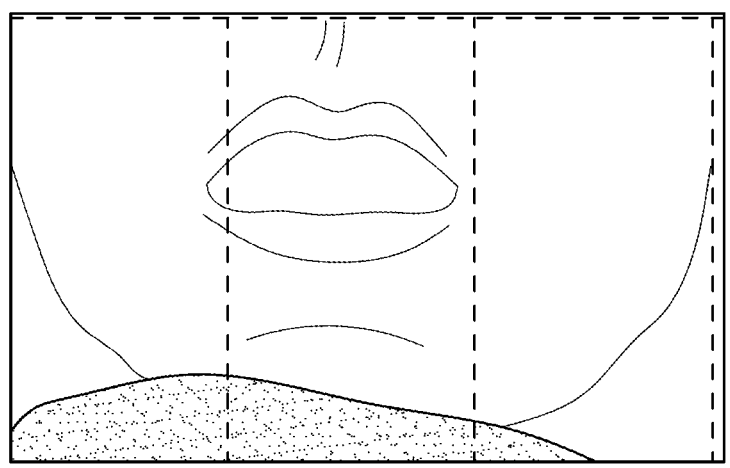
FIG. 5 is a schematic diagram of a mouth portion image of the mouth and nose occluded detecting method according to the embodiment of FIG. 1.

FIG. 4 is a schematic diagram of a nine-square facial portion image 300 of the mouth and nose occluded detecting method s100 according to the embodiment of FIG. 1. FIG. 5 is a schematic diagram of a mouth portion image 310 of the mouth and nose occluded detecting method s100 according to the embodiment of FIG. 1. In FIG. 4 and FIG. 5, the image extraction can utilize a nine-square division so as to obtain a nine-square facial portion image 300, and the mouth portion image 310 is obtained by extracting a three-square image from a lower part of the nine-square facial portion image 300. The mouth portion image 310 is entered into the occluded convolutional neural network so as to produce the determining result. An influence of environment factor is decreased by entering the mouth portion image 310 which extracts from the image into the occluded convolutional neural network so as to avoid a misjudgment generated by the occluded convolutional neural network.

Because of the difference of a size of the facial of each person, the mouth and nose occluded detecting method s100 can further includes normalized processing the mouth portion image 310 for obtaining a post-normalizing mouth portion image, so that the misjudgment of the mouth and nose occluded detecting method s100 due to the difference of the size of the facial can be avoided. Table 5 shows an accuracy rate of an occluded convolutional neural network of a third example and an accuracy rate of an occluded convolutional neural network of a seventh comparative example, an eighth comparative example, a ninth comparative example and a tenth comparative example, respectively. A size of a post-normalizing mouth portion image of the third example is 50×50, a size of a post-normalizing mouth portion image of the seventh comparative example is 25×25, a size of a post-normalizing mouth portion image of the eighth comparative example is 75×75, a size of a post-normalizing mouth portion image of the ninth comparative example is 100×100 and a size of a post-normalizing mouth portion image of the tenth comparative example is 150×150. In Table 5, the accuracy rate of the occluded convolutional neural network of the third example is greater than the accuracy rate of the occluded convolutional neural network of the seventh comparative example, the eighth comparative example, the ninth comparative example and the tenth comparative example, respectively. In the other words, when the size of the post-normalizing mouth portion image is 50×50, the accuracy rate of the occluded convolutional neural network is increased.

TABLE 5

| | Accuracy rate |
|---|---|
| Seventh comparative example | 91% |
| Eighth comparative example | 90% |
| Ninth comparative example | 89% |
| Tenth comparative example | 85% |
| Third example | 94% |

Figure 6:
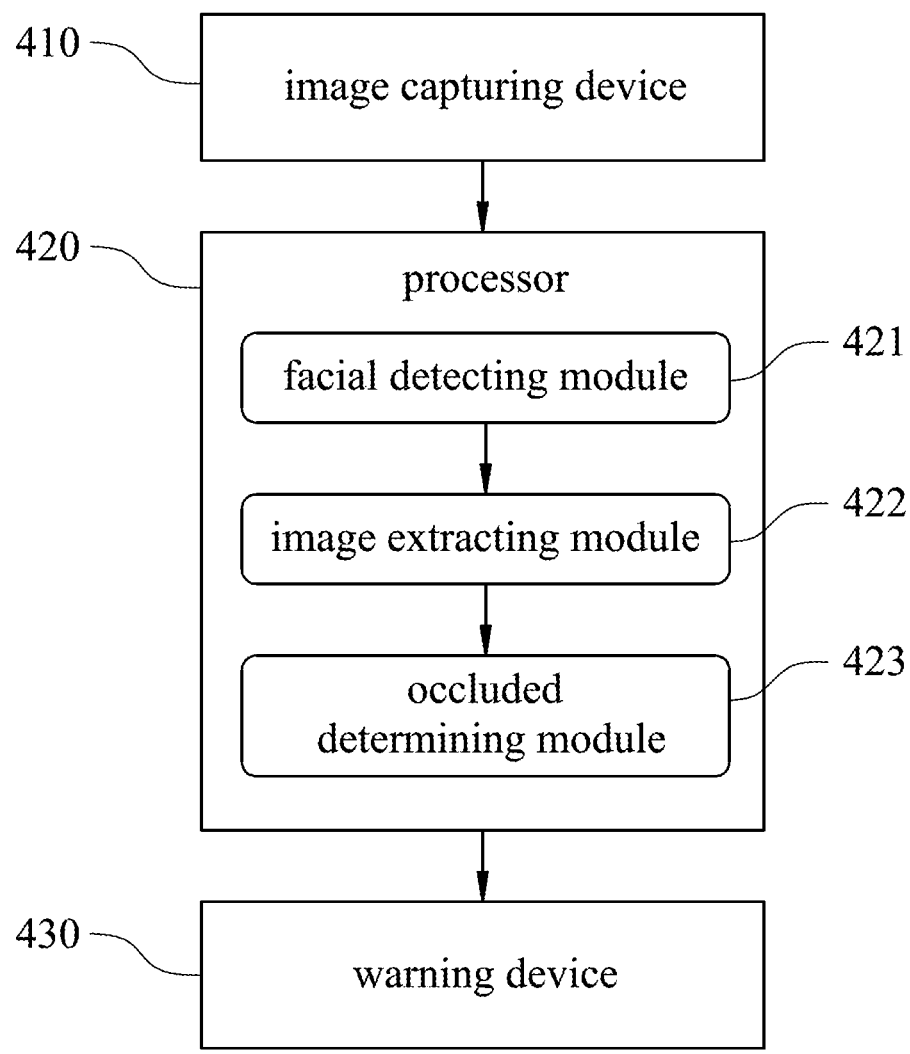
FIG. 6 is a block diagram of a mouth and nose occluded detecting system according to one embodiment of the present disclosure.

FIG. 6 is a block diagram of a mouth and nose occluded detecting system 400 according to one embodiment of the present disclosure. In FIG. 6, the mouth and nose occluded detecting system 400 includes an image capturing device 410, a processor 420 and a warning device 430. The image capturing device 410 is for capturing an image. The processor 420 is electronically connected to the image capturing device 410, and includes a facial detecting module 421, an image extracting module 422 and an occluded determining module 423. The facial detecting module 421 is electronically connected to the image capturing device 410, wherein the facial detecting module 421 captures the image by the image capturing device 410, and a facial portion image is obtained from the image according to a facial detection. The image extracting module 422 is electronically connected to the facial detecting module 421, wherein the image extracting module 422 extracts a mouth portion from the facial portion image according to an image extraction so as to obtain a mouth portion image 310. The occluded determining module 423 is electronically connected to the image extracting module 422, wherein the occluded determining module 423 enters the mouth portion image 310 into an occluding convolutional neural network so as to produce a determining result. The warning device 430 is signally connected to the processor 420, wherein the warning device 430 provides a warning according to the determining result. When the determining result is a normal state, a determining step s110 is performed. When the determining result is an occluding state, the warning is provided.

In detail, the image capturing device 410 is for capturing an image of the patient so as to produce the image, wherein the image capturing device 410 is camera. The facial detecting module 421 of the processor 420 is for obtaining the facial portion image from the image by the facial detection, wherein the facial detection utilizes a Multi-task cascaded convolutional network for detecting a facial portion of the image. The image extracting module 422 of the processor 420 extracts the mouth portion from the facial portion image by an image extraction so as to obtain the mouth portion image 310, wherein the image extraction utilizes a nine-square division so as to obtain a nine-square facial portion image 300, and the mouth portion image 310 is obtained by extracting a three-square image from a lower part of the nine-square facial portion image 300. The occluded determining module 423 of the processor 420 is for producing the determining result by entering the mouth portion image 310 into the occluding convolutional neural network, wherein the determining result is the occluding state or the normal state. The processor 420 is a micro-processor, a central processing unit or other electronic processing unit. The warning device 430 provides the warning according to the determining result. When the determining result is the normal state, the image capturing device 410 captures the image of the patient again and monitor a state of a patient, continuously. When the determining result is the occluding state, the warning is provided so as to notify a protector to treatment, expeditiously. The warning device 430 is an image warning (flashing light) or a voice warning (buzzer). The mouth and nose occluded detecting system 400 can be applied to a computer or a cell phone.

In order to improve an accuracy rate of the mouth and nose occluded detecting system 400, the occluded convolutional neural network can include six convolutional layers, three pooling layers, a hidden layer h1 and an output layer op, wherein the occluded convolutional neural network structure 200 is the same with FIG. 3, Table 2, Table 3 and Table 4, and will not be described again herein.

Hence, the mouth and nose occluded detecting method and the mouth and nose occluded detecting system can provide the following advantages:

(1) The accuracy rate of the occluded convolutional neural network can be increased by increasing the number of the training samples of the occluded convolutional neural network via the image procession.

(2) An influence of environment factor is decreased by entering the mouth portion image into the occluded convolutional neural network so as to avoid the occluded convolutional neural network provides a misjudgment and increases the accuracy rate of the occluded convolutional neural network.

(3) The mouth and nose occluded detecting method and the mouth and nose occluded detecting system utilize the occluded convolutional neural network structure so as to increase the accuracy rate of the occluded convolutional neural network.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A mouth and nose occluded detecting method, comprising:
   a detecting step, comprising:
      a facial detecting step, wherein an image is captured by an image capturing device, and a facial portion image is obtained from the image according to a facial detection;
      an image extracting step, wherein a mouth portion is extracted from the facial portion image according to an image extraction so as to obtain a mouth portion image; and
      an occluded determining step, wherein the mouth portion image is entered into an occluding convolutional neural network so as to produce a determining result, and the determining result is an occluding state or a normal state; and
   a warning step, wherein a warning is provided according to the determining result, when the determining result is the normal state, the detecting step is performed; when the determining result is the occluding state, the warning is provided;
   wherein the occluding convolutional neural network comprises a softmax layer, the softmax layer comprises at least one image state, the mouth portion image, at least one image state parameter, at least one image state probability and an image state probability set, the softmax layer is corresponded by:

$$h_\theta(x^{(i)}) = \begin{bmatrix} p(y^{(i)} = 1 \mid x^{(i)}; \theta) \\ p(y^{(i)} = 2 \mid x^{(i)}; \theta) \\ \vdots \\ p(y^{(i)} = k \mid x^{(i)}; \theta) \end{bmatrix} =$$

$$\frac{1}{\sum_{j=1}^{k} e^{\theta_j^T x^{(i)}}} \begin{bmatrix} e^{\theta_1^T x^{(i)}} \\ e^{\theta_2^T x^{(i)}} \\ \vdots \\ e^{\theta_k^T x^{(i)}} \end{bmatrix};$$

wherein $y^{(i)}$ is the at least one image state, k is a number of the image state, $x^{(i)}$ is the mouth portion image, $\theta_1, \theta_2, \ldots, \theta_K$ are the image state parameters, $p(y^{(i)} = k \mid x^{(i)}; \theta)$ is the image state probability, $h_\theta(x^{(i)})$ is the image state probability set and T means transpose matrix.

2. The mouth and nose occluded detecting method of claim 1, further comprising:
   a module establishing step, comprising:
      a database establishing step, wherein an occluding detection database is established, and the occluding detection database comprising a plurality of occluding images and a plurality of normal images;
      an image processing step, wherein a post-processing occluded detection image is obtained from each of the occluding images or each of the normal images according to an image procession, and the post-processing occluded detection image is stored into the occluding detection database; and
      a data training step, wherein the occluding convolutional neural network is trained by the post-processing occluded detection images, the occluding images and the normal images in the occluding detection database.

3. The mouth and nose occluded detecting method of claim 2, wherein the image procession is an image flipping, a histogram equalization, a log transform, a gamma processing or a Laplace processing.

4. The mouth and nose occluded detecting method of claim 1, wherein the occluding convolutional neural network comprises six convolutional layers, three pooling layers, a hidden layer and an output layer.

5. The mouth and nose occluded detecting method of claim 4, wherein each of the convolutional layers comprises a plurality of kernels, a size of each of the kernels is 3×3 and a stride of each of the kernels is 1.

6. The mouth and nose occluded detecting method of claim 4, wherein an output of each of the convolutional layers is a plurality of feature maps, and each of the convolutional layers adjusts a size of each of the feature maps according to a padding method.

7. The mouth and nose occluded detecting method of claim 4, wherein each of the pooling layers utilizes a max pooling method and comprises a pooling filter, a size of the pooling filter is 2×2 and a stride of the pooling filter is 2.

8. The mouth and nose occluded detecting method of claim 4, wherein the hidden layer comprises a fully connecting layer, and a neuron number of the fully connecting layer is 128.

9. The mouth and nose occluded detecting method of claim 1, wherein a nine-square facial portion image is obtained from the facial portion image according to a nine-square division, and the mouth portion image is obtained by extracting a three-square image from a lower part of the nine-square facial portion image.

10. The mouth and nose occluded detecting method of claim 1, wherein the facial detection utilizes a Multi-task cascaded convolutional network for detecting a facial portion of the image.

11. A mouth and nose occluded detecting system, comprising:
- an image capturing device for capturing an image;
- a processor electronically connected the image capturing device, and comprising:
  - a facial detecting module electronically connected the image capturing device, wherein the facial detecting module captures the image by the image capturing device, and a facial portion image is obtained from the image according to a facial detection;
  - an image extracting module electronically connected the facial detecting module, wherein the image extracting module extracts a mouth portion from the facial portion image according to an image extraction so as to obtain a mouth portion image; and
  - an occluded determining module electronically connected the image extracting module, wherein the occluded determining module enters the mouth portion image into an occluding convolutional neural network so as to produce a determining result; and
- a warning device signally connected the processor, wherein the warning device provides a warning according to the determining result, when the determining result is a normal state, a determining step is performed; when the determining result is an occluding state, the warning is provided;

wherein the occluding convolutional neural network comprises a softmax layer, the softmax layer comprises at least one image state, the mouth portion image, at least one image state parameter, at least one image state probability and an image state probability set, the softmax layer is corresponded by:

$$h_\theta(x^{(i)}) = \begin{bmatrix} p(y^{(i)} = 1 \mid x^{(i)}; \theta) \\ p(y^{(i)} = 2 \mid x^{(i)}; \theta) \\ \vdots \\ p(y^{(i)} = k \mid x^{(i)}; \theta) \end{bmatrix} = \frac{1}{\sum_{j=1}^{k} e^{\theta_j^T x^{(i)}}} \begin{bmatrix} e^{\theta_1^T x^{(i)}} \\ e^{\theta_2^T x^{(i)}} \\ \vdots \\ e^{\theta_k^T x^{(i)}} \end{bmatrix};$$

wherein $y^{(i)}$ is the at least one image state, k is a number of the image state, $x^{(i)}$ is the mouth portion image, $\theta_1, \theta_2, \ldots, \theta_K$ are the image state parameters, $p(y^{(i)} = k \mid x^{(i)}; \theta)$ is the image state probability, $h_\theta(x^{(i)})$ is the image state probability set and T means transpose matrix.

12. The mouth and nose occluded detecting system of claim 11, wherein image capturing device is camera.

13. The mouth and nose occluded detecting system of claim 11, wherein the occluding convolutional neural network comprising six convolutional layers, three pooling layers, a hidden layer and an output layer.

14. The mouth and nose occluded detecting system of claim 11, wherein the facial detecting is a Multi-task cascaded convolutional network so as to detect a facial portion of the image.

* * * * *